United States Patent [19]

Terao et al.

[11] 3,984,401

[45] Oct. 5, 1976

[54] PROCESS FOR PRODUCING LACTOL-TYPE CEPHALOSPORINS

[75] Inventors: Shinji Terao, Toyonaka; Mitsuru Shiraishi, Suita; Toshio Miyawaki, Nishinomiya; Isao Minamida, Kyoto; Masayoshi Yamaoka, Higashiyodogawaku; Yoshio Imashiro, Nishinomiya; Mitsuo Numata, Takatsuki, all of Japan

[73] Assignee: Takeda Chemical Industries, Ltd., Japan

[22] Filed: Dec. 7, 1973

[21] Appl. No.: 422,748

[30] Foreign Application Priority Data

Dec. 8, 1972 Japan............................. 47-123601
Dec. 25, 1972 Japan............................. 47-1423

[52] U.S. Cl............................. 260/243 C; 424/246
[51] Int. Cl.²......................................... C07D 515/14
[58] Field of Search ............................. 260/243 C

[56] References Cited
UNITED STATES PATENTS 3,351,596  11/1967  Chamberlin.................... 260/243 C
3,682,903  8/1972  Bickel......................... 260/243 C OTHER PUBLICATIONS
Houben–Weyl, *Methoden Der Organischen Chemie*, Band VI/2, 1963, p. 716.

*Primary Examiner*—Nicholas S. Rizzo
*Assistant Examiner*—Mary C. Vaughn
*Attorney, Agent, or Firm*—Craig & Antonelli

[57] ABSTRACT

A 3-hydroxymethylcephalosporin which is not protected at the carboxyl group can be directly oxidized with a hexavalent chromium compound to give in good yield a lactol type cephalosporin represented by the general formula:

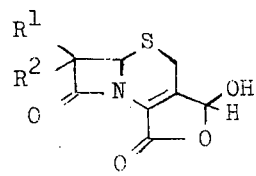

wherein $R^1$ is hydrogen or an alkoxy group and $R^2$ is an acylamino, or imido group. The resulting compounds are very useful and important as intermediates for preparing, e.g. 3-alkoxyiminomethyl cephalosporins.

29 Claims, No Drawings

PROCESS FOR PRODUCING LACTOL-TYPE CEPHALOSPORINS

This invention relates to a novel process for producing a lactol-type cephalosporin of the general formula:

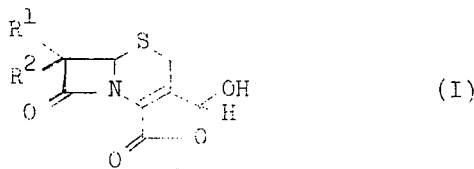

wherein $R^1$ is hydrogen or an alkoxy group and $R^2$ is an acylamino or imido group, by the oxidation of a 3-hydroxymethyl-4-carboxyl cephalosporin.

These compounds are not only per se antimicrobial but also useful for further synthesis of cephalosporin derivatives.

Although various methods have been presented for the production of 3-formyl-3-cephem-4-carboxylic acid esters, . . . most of which comprises oxidation of the corresponding 3-hydroxymethyl esters as shown by, for example, USP3,351,596, U.S. Pat. No. 3,682,903, German Offenlegungschrift 2128605 and Journal of the Medicinal Chemistry 10, 966, (1967) . . . , there has been no advantageous method for producing compound (I) which is a hydrolyzed form of the above-mentioned esters.

Although one might think of the possibility that the hydrolysis of the 3-formyl 3-cephem-4-carboxylic acid esters could afford the compounds (I), it is practically disadvantageous, because, when esterification of 3-formyl-3-cephem-4-carboxylic acids is intended without causing transition of the double bond from $\Delta^3$ to $\Delta^2$, it can be conducted only with diazo-compounds such as diazomethane, diazoethane, diphenyldiazomethane, phenyldiazoethane. To make the matter worse the hydrolysis of the esters needs so drastic conditions as inevitably accompany degradation of the esters leading to complex results.

Even if the esterification is started from 3-acetoxymethyl-3-cephem-4-carboxylic acids followed by selective hydrolysis of 3-acetoxy group, selective oxidation of 3-hydroxymethyl group and hydrolysis of 4-carboxylic acid ester, those difficulties as mentioned above cannot be avoided.

A possible alternative method is the isomerization of a 7-phenylacetylamino-3-formyl-2-cephem-4-carboxylic acid (U.S. Pat. No. 3,682,903), but this is not advantageous since the yield of the starting material to be prepared from a commercially available compound and the yield of transition reaction are both very low.

Under these circumstances the present inventors conducted an extensive research and have ultimately discovered that when a compound of the general formula:

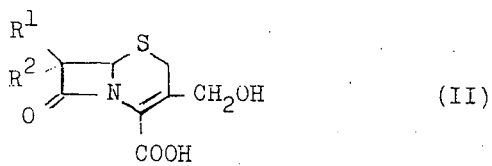

(wherein $R_1$ and $R_2$ are as previously defined) or a salt thereof is oxidized with a hexavalent chromium compound, the oxidation reaction proceeds with readiness and gives rise the contemplated compounds (I) in excellent yields. This invention is the culmination of the above findings.

In general formula (II), $R^1$ is hydrogen or a lower alkoxy group such as methoxy, ethoxy, etc.; $R^2$ is an amino group which has been acylated by an acyl group which may be found in the corresponding moiety of cephalosporin or penicillin compounds. Thus, for example, the amino groups acylated by aliphatic carboxylic acid acyl groups such as hexanoyl, propionyl, heptanoyl, cyclopentanoyl, etc., monosubstituted acetyl groups such as phenylacetyl, cyclohexylacetyl, thienylacetyl, tetrazolylacetyl, cyanoacetyl, phenoxyacetyl, nitrophenylacetyl, phenylthioacetyl, phenethylthioacetyl, allylthioacetyl, benzylthiopropionyl, etc., di-substituted acetyl groups such as α-carboxyphenylacetyl, α-bromopropionyl, α-sulfothienylacetyl, α-sulfophenylacetyl, α-hydroxyphenylacetyl, α-phenoxybutyloyl, phenylglycyl, cyclohexenylglycyl, thienylglycyl, furylglycyl, phenylmethylglycyl, carbamoylphenylacetyl, 5-amino-5-carboxyvaleryl, N-protected 5-amino-5-carboxyvaleryl such as 5-benzoylamino-5-carboxyvaleryl, 5-(isobornyloxycarbonyl)-amino-5-carboxyvaleryl, α-(β-methylsulfonylethoxycarbonyl)-aminophenylacetyl, 5-(β-methylsulfonylethoxycarbonyl)amino-5-carboxyvaleryl, 5-(phenylacetyl)amino-5-carboxyvaleryl, 5-(p-(t-butyl)-benzoylsulfonyl)amino-5-carboxyvaleryl, 5-tosylamino-5-carboxyvaleryl, 5-p-(t-butyl)-benzoylamino-5-carboxyvaleryl, etc., acryl group, aromatic acyl groups such as benzoyl, 2,6-dimethoxybenzoyl, etc., heterocyclic acyl groups such as 5-methyl-3-phenyl-4-isoxazolylcarbonyl, 3-0-chlorophenyl-5-methyl-4-isoxazolylcarbonyl, etc., and so on. $R^2$ may alternatively be an imido group such as phthalimido, succinimido, maleinimido, etc. The starting compound (II) to be employed in this invention is subjected to the oxidation either in the form of free acid or in the form of salt thereof. The salt of the compounds (II) are more commonly an alkali metal salt, e.g. sodium or potassium salt, although the salt of an organic base that would not have a specially adverse effect upon the oxidation reaction, such as triethylamine, pyridine and so on.

The method of this invention is practiced by permitting a hexavalent chromium compound to act upon a compound (II) in the presence of a solvent. The solvents which may routinely be employed include, among others, an organic solvents such as acetone, acetonitrile, tetrahydrofuran, ethyl acetate, chloroform, dichloromethane, ether, dioxane, dimethylformamide, dimethylacetamide, acetic acid and mixtures of such solvents. These solvents are desired to be substantially anhydrous.

The hexavalent chromium compound may for example be chromic anhydride, t-butyl chromate, chromyl acetate or chromyl chloride. To promote the oxidation reaction, the oxidizing agent is employed in combination with an acid such as sulfuric acid, phosphoric acid or glacial acetic acid. It should be noticed, however, that since the use of an acid in excess may induce the lactonization, it is desirable, when the starting compound (II) is used in the form of a salt, to employ the acid not to exceed the amount necessary for the salt to become the free carboxylic acid. Thus, since the lactonization reaction proceeds fast in a pH near or below the pKa (near 2.90) of the 4-carboxylic acid, it is desirable to maintain the pH of the reaction mixture near the pKa of the 4-carboxylic acid. Thus, when a salt of starting compound (II) is employed, for instance, the ratio of hexavalent chromium compound (per oxidation equivalent): acid (per mole): compound to be oxidized (II) (per mole) is preferably 2:1:1 when the compound to be oxidized (II) is a monobasic carboxylic acid or 2:2:1 when said compound (II) is a dibasic acid. That is to say, the ratio is generally expressed as 2:n:1, wherein n is the number of the acid group involved in the starting compound (II). Thus, satisfactory results are obtained when the hexavalent chromium compound is permitted to act upon the salt of the starting compound (II) in the presence of a sufficient amount of acid to convert the salt to the free carboxylic acid. When compound (II) is used in the form of free carboxylic acid, it is necessary to react the hexavalent chromium compound while the pH of the reaction mixture is maintained at a value near the pKa of the 4-carboxylic acid. For the purpose, the hexavalent chromium compund per oxidation equivalent is used 2 times of the starting compound (II) (per mole).

Further, the compound (II) is oxidized preferably in a state of salt with sodium or potassium and the salt is suspended in finely divided state in the reaction solvent. The hexavalent chromium compound is preferably dissolved in the reaction solvent which contains a small amount of water necessary for dissolving it. As the water, moisture contained in the reaction system, namely moisture in e.g. an acid, solvent, hexavalent chromium compound, etc. may be sufficient.

Generally, the reaction may be conducted at room temperature under cooling with ice, preferably at 0° to 30°C, and goes to conclusion generally within a relatively short period of time, say, about 10 minutes.

The reaction mixture thus obtained contains the contemplated compound (I) which, depending upon the solvent polarity and pH of the medium, may exist either in the form of 3-formyl-4-carboxylic acid of general formula (III):

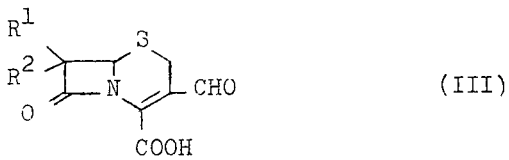

(wherein $R^1$ and $R^2$ are as previously defined), which is a tautomer of the lactol form (I), or in an equilibrium mixture of forms (I) and (III). For example, in water, ethanol or methanol at pH above about 3.0, the compounds prefer 3-formylcarboxylic acid form (III), while at pH of about 2.0 or less, they prefer the lactol form (I) in the same solvents. The nuclear magnetic resonance spectrum of the free acid of 3-formylcephalosphorins in $d_6$-dimethylsulfoxide reveals that they take the lactol form (I) predominantly, while the ultraviolet absorption spectrum of the same compounds in ethanol shows that they exist mainly in the 3-formylcarboxylic acid form (III). This is the evidence of an equilibrium relation between forms (I) and (III).

When a compound is in the 3-formyl-carboxylic acid form (III), it is too unstable to be isolated by routine procedures due to unstableness of the free formyl and β-lactam groups. On the other hand when the compound is in the lactol form (I), it is stable enough to be separated by routine procedures.

Therefore, on isolation of the compound, one might adjust the pH of the reaction mixture to 2–7 (preferably about 2.5 to 4) to keep the product in a stable lactol form (I) and then extract the reaction mixture with an organic solvent such as ethyl acetate, butyl acetate, methyl isobutyl ketone or the like. The extract may usually be purified by, for example evaporation, recrystallization. Besides the above procedures, the compound can be purified by such routine procedures as liquid chromatography, thin layer chromatography and so forth.

The compound (I) is treated with an alcohol such as methanol, ethanol, propanol and butanol in the presence of an acid or with an acylating agent such as acetylchloride, acetylbromide and acetic anhydride, whereby the lactol hydroxyl group of the compound (I) is substituted by an alkoxy or an acyloxy group.

The starting compound (II) or salt thereof can be prepared by the removal of the acetyl group from the compounds of the general formula:

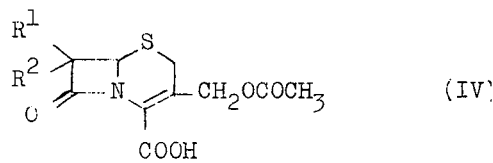

(wherein $R^1$ and $R^2$ are as previously defined), the removal of the acetyl group being effected by enzymatic or chemical hydrolysis of the compounds of the above general formula. Among them, 3-desacetylcephalosporin C can be directly obtained from fermentation processes and can be used as a starting material in the oxidation reaction.

The product compounds (I) are antibiotic against penicillin-sensitive or penicillin-resistant strains of *Micrococcus pyrogenes var. aureus, pneumobacillus* and *typhoid bacillus*. Therefore, these compounds can be used, for example, as drugs or bactericides for the purpose of preventing infections due to said microorganisms or as food additives for the purpose of preserving nutrients: For these purposes, the dosage, preparation form and so on may easily be determinable through routine and established manner in antibiotic technology.

Furthermore, the product compound (I) or alkoxy or acyloxy derivatives thereof are of use as intermediates for the production of other cephalosporin compounds. For example, they are reacted with amino compounds, e.g. hydrazine, the hydrazines of alkyl, aryl or heterocyclic compounds such as methyl hydrazine, ethyl hydrazine, isopropyl hydrazine, phenyl hydrazine, p-nitrophenyl hydrazine, 3,5-dimethyl hydrazine, pyridyl hydrazine, thienyl hydrazine, 1-amino-4-methyl hydrazine, etc.; acyl hydrazines having aliphatic, aromatic or heterocyclic carboxylic acid acyl groups such as acetyl, propionyl, butylyl, valeryl, benzoyl, toluoyl, salicyloyl, cinnamoyl, picolyl, thienylacetyl, phenylacetyl, phenylthioacetyl, phenyl propionyl, pyridylthioacetyl, cyanoacetyl, cyclohexylacetyl, α-hydroxyphenylacetyl, etc.; thiosemicarbazides such as thiosemicarbazide, phenylthiosemicarbazide, ethylthiosemicarbazide, acetylthiosemicarbazide, chlorophenylthiosemicarbazide, etc.;

aminoguanidine and its derivatives; hydroxylamines such as hydroxylamine, o-methylhydroxylamine, o-acetylhydroxylamine, o-isopropoxyhydroxylamine, hydroxylamine-o-sulfonic acid, etc.; primary alkyl, allyl, aryl, heterocyclic amines, e.g. ethylamine, propylamine, allylamine, cyclohexylamine, aniline, p-nitroaniline, o,p-dinitroaniline, o-chloroaniline, naphthylamine, pyridylamine, thienylamine, 4-methylpiperazylamine, furylamine, etc.; and N-imines, e.g. pyridine N-imine, quinoline N-imine, etc. in a solvent, e.g. water, methanol, ethanol, etc. in the presence of an acid catalyst, e.g. sulfuric acid, hydrochloric acid, etc., to obtain the substituted iminomethyl compound represented by the general formula:

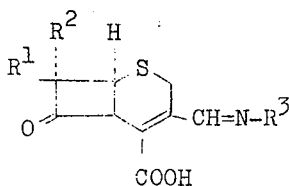

(V)

wherein $R^1$ and $R^2$ are as defined above, $R^3$ is hydrogen, hydroxyl, amino, $-OSO_3H$ or an organic residue. The compound (V) have excellent characteristics as antibiotics, e.g. activity against Gram-positive, Gram-negative and penicillin resistant bacteria and may be used in a manner similar to that of the compound (I).

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g.", "mg.", "ml.", "cm.", "Hz", "MHz", "mm", "m.p." and "decomp." are abbreviations of "gram", "milligram", "milliliter", "centimeter", "Hertz", "megahertz", "nonameter", "melting point" and "decomposed", respectively; all the temperatures are uncorrected and the percentages are all on the weight basis except specifically defined.

The NMR spectra in the examples to be given hereinafter were measured using a Varian T60 or a HA100 spectrometer, with tetramethylsilane as an internal reference. The δ values were expressed in p.p.m. Unless otherwise specified, deuteriochloroform was used as the solvent. The symbol s signifies a singlet, d a doublet, t a triplet, q a quartet, AB q a AB type quartet, m a multiplet and J a coupling constant in Hz.

EXAMPLE 1

1. N-Isobornyloxycarbonyl-deacetylcephalosporin C disodium.

To cephalosporin C monosodium (47.4 g.) are added water (500 ml.) and acetone (150 ml.) and the resultant mixture is maintained at 3°–4°C. While the mixture is stirred, its pH is adjusted to 9.0 by the addition of sodium carbonate powder and, then, isobornyl chlorocarbonate (43.3 g.) is added dropwise over a period of 1.5 hour. Throughout this period, sodium carbonate powder is added from time to time to maintain the pH of the system at 9.0. The mixture is stirred at 3°–4°C and pH 9.0 for another 1.5 hour. Thereafter, the pH is brought to 7.0 by the addition of phosphoric acid and a major portion of the acetone is distilled off under reduced pressure. The concentrate is washed twice with ethyl acetate (400 ml.) and the water layer is cooled to 5°C and, under stirring, adjusted to pH 2.5 with phosphoric acid. It is then extracted with ethyl acetate (600 ml.) three times. The extract is dried over anhydrous sodium sulfate and, then, concentrated to dryness under reduced pressure. The procedure yields N-isobornyloxycarbonyl-cephalosporin C (55.4 g.).

2. The N-isobornyloxycarbonyl-cephalosporin C (5.96 g.) is made into the disodium salt by the addition of water (20 ml.) and sodium bicarbonate (1.68 g.). To this aqueous solution are added phosphate buffer (pH 7.2; 100 ml.) and lipase originated from Rhizopus NR400, manufactured by Osaka Saikin Kenkyusho under the tradename "Saiken 100" (9.54 g.). At a constant temperature of 30°C and with the pH being held at about 7.2, the system is stirred for 16 hours. The reaction mixture is then filtered under suction using diatomaceous earth manufactured by Johns-Manville Sales Corp. under the tradename "Hyflo-Super-Cel" as filter aid and the filtrate is concentrated by lyophilization. The concentrate is run onto a column of polystyrenedivinylbenzene-copolymer manufactured by Lorm and Hass under the tradename "Amberlite XAD-2". The column is first irrigated with water and, then, with 5% aqueous ethanol (v/v). The fractions containing the product compound are pooled and concentrated under reduced pressure to remove the ethanol.

Then, the concentrate is lyophilized to obtain N-isobornyloxycarbonyl-deacetylcephalosporin C disodium (4.87 g.), melting point: 165°–170°C(decomp.)

Nuclear magnetic resonance spectrum($D_2O$): δ 4.43(2H,s, 3-$CH_2OH$), 5.26(1H,d, J=5Hz, 6-H), 5.77(1H,d, J=5Hz, 7-H).

Infrared absorption spectrum (KBr disc): 1760(β-lactam ring), 1599$cm^{-1}$(—$CO_2Na$).

Ultraviolet absorption spectrum: $\lambda_{max.}^{H_2O}$ 261.5nm; $\lambda_{min.}^{H_2O}$ 225.5nm.

3.

7-β-[D-5-(isobornyloxycarbonyl)amino-5-carboxyvaleramido]-3-formyl-3-cephem-4-carboxylic acid Acetone (80 ml.) is added to N-isobornyloxycarbonyl-deacetylcephalosporin C disodium (2.99 g.) and the resultant suspension is stirred under cooling at 5°C. Then, 1.88 ml. of a solution (hereafter referred to briefly as reagent B) composed of chromic anhydride (2.67 g.; choice grade), concentrated sulfuric acid (5.52 ml., $H_2SO_4$ 1.77 g./ml.) and water (to make 15.0 ml.) is added dropwise over a period of 3 minutes, followed by stirring for a further 20 minutes at 5°C. After the reaction has been completed, a major portion of the acetone is distilled off, followed by the addition of water (30 ml.). The solution is extracted with ethyl acetate (50 ml.) three times. The ethyl acetate layer is dried over anhydrous sodium sulfate and, then, evaporated to dryness under reduced pressure. The procedure yields 7-β-(D-5-(isobornyloxycarbonyl)amino-5-carboxyvaleramido)-3-formyl-3-cephem-4-carboxylic acid (2.06 g.). Nuclear magnetic resonance spectrum ($d_6$-dimethylsulfoxide + $D_2O$): δ 5.07(1H,d, J=5Hz, 6-H), 5.75(1H,d, J=5Hz, 7-H), 6.23(1H,s, 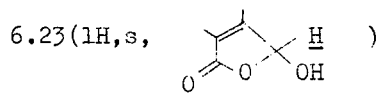 )

Infrared absorption spectrum (KBr disc): 1797cm$^{-1}$($\beta$-lactam ring).

Ultraviolet absorption spectrum: $\lambda_{max}^{H_2O}$ 300 nm; $\lambda_{min}^{H_2O}$ 238 nm $\lambda_{max}^{H_2O-H\,SO}$ 260 nm; $\lambda_{min}^{H_2O-H\,SO_2}$ 233nm.

The nuclear magnetic resonance spectrum of this product in d$_6$-dimethylsulfoxide reveals that it takes the lactol form which is a tautomer of the 3-formyl-carboxylic acid, while the ultraviolet absorption spectrum of the same in aqueous solution suggests that it takes the 3-formyl-carboxylic acid form. The ultraviolet absorption spectrum of the same product in diluted sulfuric acid solution indicates that it exists in the lactol form.

EXAMPLE 2

1. N-Phenylacetyl-deacetylcephalosporin C disodium

A. Cephalosporin C monosodium (4.20 g.) is dissolved in water (50 ml.) and the solution is maintained at 3°C, with stirring. The solution is adjusted to pH 8.5 with sodium carbonate powder, followed by the gradual addition of a solution of phenylacetyl chloride (1.60 g.) in acetone (10 ml.). After the dropwise addition has been completed, with the pH being held at 8.5, the mixture is further stirred under the same conditions for 2 hours.

The reaction mixture is adjusted to pH 7.20 with phosphoric acid and concentrated under reduced pressure to about 30 ml.

To this concentrate is added phosphate buffer to bring the pH to 7.20 and the volume to 70 ml.

To this solution is added lipase "Saiken 100" (5.0 g.) and while the liquid temperature is held at 30°C, the system is stirred for 20 hours. After the reaction, the insolubles are filtered off and the filtrate is concentrated under reduced pressure to about 15 ml. The concentrate is chromatographed on a column of Amberlite XAD-2, which is irrigated with water to remove the enzyme and inorganic salt and, then, with a 1% aqueous solution of ethanol.

The eluate is lyophilized to harvest a white finely divided powder of N-phenylacetyl-deacetylcephalosporin C disodium (3.82 g.).

Nuclear magnetic resonance spectrum (D$_2$O): δ2.1–1.5(4H), 2.5–2.3 (2H), 3.45 and 3.72(2H, J=18 Hz, 2-H), 3.74(2H), 4.28(1H, t), 4.38(2H, 3-CH$_2$OH), 5.17(1H, d, J=4Hz), 5.68(1H, d, J=4Hz), 7.47(5H).

B. Deacetylcephalosporin C monosodium (3.72 g.) is dissolved in water (40 ml.) and while the solution is stirred at a constant temperature of 3°C, its pH is adjusted to 8.5 with sodium carbonate. To this solution is then added, dropwise, a solution of phenylacetyl chloride (1.60 g.) in acetone (10 ml.). After the dropwise addition has been completed, the mixture is further stirred under the same conditions for 2 hours. After the reaction, the mixture is adjusted to pH 7.0 with phosphoric acid and concentrated under reduced pressure to 15 ml. The concentrate is chromatographed on a column of Amberlite XAD-2 resin (500 ml.). The column is irrigated with water and, then, with a 1% aqueous solution of ethanol (v/v). The eluate is lyophilized to harvest a white finely-divided powder of N-phenylacetyl-deacetylcephalosporin C disodium (4.18 g.). This product was identified with the N-phenylacetyl-deacetylcephalosporin C disodium sample prepared by the above A method by comparing their infrared absorption spectra.

2. 7-$\beta$-(5-carboxy-5-phenylacetylaminobutyramido)-3-formyl-3-cephem-4-carboxylic acid In acetone (10 ml.) is suspended N-phenylacetyl-deacetyl-cephalosporin C disodium (510 mg.) and the mixture is cooled to 5°C with ice under stirring. To this suspension is added the reagent B according to Example 1 (0.375 ml.) over a period of 10 minutes and, then, the reaction mixture is concentrated under reduced pressure. To the residue is added water (10 ml.), followed by extraction with 3 portions of ethyl acetate (30 ml.). The organic layers are pooled, washed with water, dehydrated (over anhydrous sodium sulfate) and concentrated. The procedure yields an almost pure sample of 7-$\beta$-(5-carboxy-5-phenylacetylaminobutramido)-3-formyl-3-cephem-4-carboxylic acid (312 mg.) in the lactol form. Nuclear magnetic resonance spectrum (d$_6$-dimethylsulfoxide):

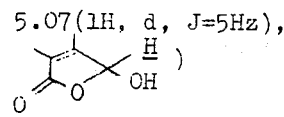

5.07(1H, d, J=5Hz), 5.76 (1H, d, J=5Hz), 6.23(1H, s,

Infrared absorption spectrum (KBr disc): 1794cm$^{-1}$($\beta$-lactam ring)

Ultraviolet absorption spectrum: $\lambda_{max}^{EtOH}$ 299 nm

The nuclear magnetic resonance spectrum of this product in d$_6$-dimethylsulfoxide indicates that the compound takes the lactol form, while the ultraviolet absorption spectrum of the same in ethanol suggests that the compound takes the formyl form.

EXAMPLE 3

1. In phosphate buffer (pH 7.2, 200 ml.) is dissolved 7-$\beta$-(2-thienylacetamido)-3-acetoxymethyl-3-cephem-4-carboxylic acid sodium salt (10.12 g.). To this solution is added lipase "Saiken 100" (10 g.) and the system is allowed to react on a water bath at 30°C for 16 hours, with constant stirring.

Throughout this period, an aqueous solution of sodium hydrogen carbonate is added to the system so that the pH will not drop below 7.2. After the reaction has been completed, the system is filtered with diatomaceous earth manufactured Johns-Manville Sale Corp. under the trade name "Celite". The filtrate is concentrated under reduced pressure to about 50 ml. and the concentrate is run onto a column of Amberlite XAD-2(5×57 cm). The column is irrigated first with 500 ml. of water and then with a 10% aqueous solution of ethanol (v/v). The eluate is lyophilized to harvest a white finely divided powder of 7-$\beta$-(2-thienylacetamido)-3-hydroxymethyl-3-cephem-4-carboxylic acid sodium (7.8 g.).

Nuclear magnetic resonance spectrum (D$_2$O): δ 3.48 and 3.72 (2H, J=18Hz), 4.00(2H, s), 4.39(2H, s), 5.17(1H, d, J=5Hz), 5.72(1H, d, J=5Hz), 7.15 (2H), 7.45 (1H).

Infrared absorption spectrum (KBr disc): 3270, 1752, 1659, 1595, 1546cm$^{-1}$.

Ultraviolet absorption spectrum: $\lambda_{max}^{H_2O}$ 235 nm (ε =11,000)

(2)

7-β-(2-Thienylacetamido)-3-formyl-3-cephem-4-carboxylic acid

In acetone (60 ml.) is suspended 7-β-(2-thienylacetamido)-3-hydroxymethyl-3-cephem-4-carboxylic acid sodium (1.128 g.). Then, under cooling with ice and stirring, 0.75 ml. of a solution (hereafter called "reagent A") composed of chromic anhydride (2.67 g., choice grade), concentrated sulfuric acid (2.26 ml.; $H_2SO_4$ content 1.77 g./ml.) and water (to make 10.0 ml.) is gradually added dropwise to the above suspension.

After the dropwise addition has been completed, the mixture is stirred under the same conditions for a further 10 minutes.

Then, the reaction mixture is concentrated and water is added to the concentrate. The mixture is extracted twice with ethyl acetate (70 ml.) and the organic layers are washed twice with water (50 ml.) dehydrated over anhydrous sodium sulfate and evaporated under reduced pressure to remove the ethyl acetate. The procedure yields 7-β-(2-thienylacetamido)-3-formyl-3-cephem-4-carboxylic acid (576 mg.).

Nuclear magnetic resonance spectrum ($d_6$-DMSO): δ 3.68 (2H), 3.74 (2H, s), 3.80–4.60 (1H, m.), 5.06 (1H, d, J=5Hz), 5.82 (1H, q, J=5 and 8 Hz), 6.23 (1H, s, (1H, d, J=5Hz),

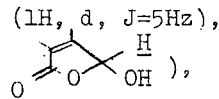

6.90 (2H), 7.29 (1H), 9.15 (1H, d, J=8Hz).

Infrared absorption spectrum (KBr disc): 1790, 1770, 1675, 1535cm$^{-1}$.

Ultraviolet absorption spectrum: $\lambda_{max}^{H_2O}$ 234 nm; $\lambda_{max}^{H_2O}$ 299.5 nm The ultraviolet absorption spectrum of this product reveals the aldehyde structure. On the other hand, the infrared and nuclear magnetic absorption spectra of the same attest to the lactol structure which is a tautomer of the aldehyde structure.

3. In methanol (25 ml.) is dissolved 7-β-(2-thienylacetamido)-3-formyl-3-cephem-4-carboxylic acid (1.00 g.), and a catalytic amount of concentrated hydrochloric acid is added. The solution is allowed to stand at room temperature for 20 minutes. The reaction mixture is then concentrated under reduced pressure and the resultant crystals are recrystallized from methanol. The procedure gives the compound (917 mg.) of the following structural formula:

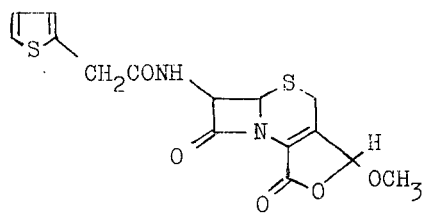

Melting point: 205°–209°C (decomp.)

Infrared absorption spectrum (KBr disc): 1795(β-lactam ring), 1663 and 1566cm$^{-1}$ (amide linkage)

Ultraviolet absorption spectrum: $\lambda_{max}^{CH_3OH}$ 236 nm (ε=12000), 260nm (ε=6500)

Nuclear magnetic resonance spectrum ($d_6$-dimethylsulfoxide, 100MHz): δ 3.50(3H, OCH$_3$), 3.65(2H, AB-pattern q, J=18Hz, 2-proton),

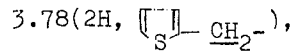

5.10 (1H, d, J=5.0Hz), 5.88(1H, q, J=5.0 and 8.0 Hz), 6.08(1H, s,

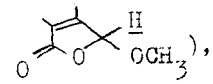

6.90(2H), 7.27(1H), 9.20(1H, J=8.0Hz, NH)

In ethanol (25 ml.) are dissolved 7-β-(2-thienylacetamido)-3-formyl-3-cephem-4-carboxylic acid (1.00 g.) and a catalytic amount of concentrated hydrochloric acid. The solution is allowed to stand at room temperature for 30 minutes. The reaction mixture is then concentrated under reduced pressure and the resultant crystals are recrystallized from a mixture of dichloromethane and ether. The procedure gives the compound (920 mg.) of the following structural formula:

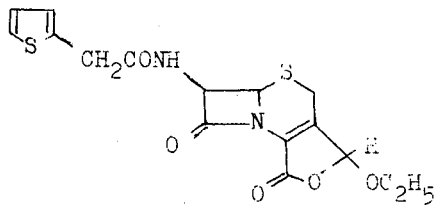

Melting point: 174°–175°C.

Infrared absorption spectrum (KBr disc): 3325, 1796, 1780, 1675, 1535cm$^{-1}$

Ultraviolet absorption spectrum: $\lambda_{max}^{EtOH}$ 236.5 nm (ε=11400), 260nm (ε=6230)

Nuclear magnetic resonance spectrum(deuteriochloroform, 100 MHz): δ 1.27(3H, t, —CH$_2$CH$_3$), 3.53(2H, s, 2-proton), 3.84(2H, s), 3.82(2H, CH$_2$CH$_3$), 4.98(1H, d, J=5.0 Hz),

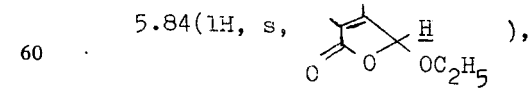

5.88(1H, q, J=5.0 and 9.0Hz), 6.64(1H, J=9.0Hz, NH), 6.96(2H), 7.20(1H)

Elementary analysis: Found: C, 50.47; H, 4.23; N, 7.13%. Calcd. (for $C_{16}H_{16}N_2O_5S_2$): C, 50.51; H, 4.24; N, 7.34%.

EXAMPLE 4

1.

7-β-[D-α-(β-Methylsulfonylethoxycarbonyl)aminophenylacetamido]-3-hydroxymethyl-3-cephem-4-carboxylic acid sodium To 7-β-(D-α-aminophenylacetamido)-3-acetoxymethyl-3-cephem-4-carboxylic acid (8.10 g.) are added water (100 ml.) and acetone (20 ml.).

This solution is cooled to 3°–4°C and, under stirring, potassium carbonate powder is added to the solution to bring its pH to 8.5. Then, a solution of β-methylsulfonylethoxycarbonyl chloride (4.48 g.) in acetone (20 ml.) is added dropwise over a period of 1 hour. During this period, potassium carbonate powder is added from time to time to maintain the pH at 8.5. Then, at a constant temperature of 3°–4°C, the reactionn mixture is further stirred for 1 hour. Then, the pH is adjusted to 7.0 with phosphoric acid and a major portion of the acetone is distilled off under reduced pressure. The concentrate is washed with ethyl acetate (100 ml.) twice and while stirring at 5°C, its pH is brought to 2.5 with phosphoric acid. The resultant precipitate is extracted with ethyl acetate (150 ml.) twice. The extracts are pooled and dried over anhydrous sodium sulfate, followed by concentration to dryness under reduced pressure. The procedure yields 7-β-[D-α-(β-methylsulfonylethoxycarbonyl)-aminophenylacetamido] -3-acetoxymethyl-3-cephem-4-carboxylic acid (10.50 g.).

This 7-β-[D-α-methylsulfonylethoxycarbonyl)aminophenylacetamido]-3-acetoxymethyl-3-cephem-4-carboxylic acid (5.00 g.) is made into the corresponding sodium salt by the addition of water (30 ml.) and sodium bicarbonate (0.756 g.).

To this aqueous solution are added phosphate buffer (pH 7.2, 100 ml.) and lipase "Saiken 100" (8.00 g.), and at a constant temperature of 30°C, the system is agitated for 13 hours, the pH being controlled at about 7.2. The resultant reaction mixture is run into a column of Amberlite XAD-2. The column is irrigated first with water and then with a 10% (v/v) aqueous solution of ethanol. The fractions containing the contemplated product are pooled and concentrated under reduced pressure to remove the ethanol. The concentrate is lyophilized to harvest 7-β-[D-α-(β-methylsulfonylethoxycarbonyl)aminophenylacetamido)-3-hydroxymethyl)-3-cephem-4-carboxylic acid sodium (3.73 g.), melting point: 166°–169°C (decomp.).

Nuclear magnetic resonance spectrum (D$_2$O): δ 3.11(3H, s, —SO$_2$CH$_3$), 4.34(2H, s, 3-CH$_2$OH), 5.12(1H), 5.42(1H), 5.76(1H), 7.36(5H).

Infrared absorption spectrum(KBr disc): 1764cm$^{-1}$ (β-lactam ring), 1602cm$^{-1}$ (—CO$_2$Na).

Ultraviolet absorption spectrum: λ $_{max}^{H_2O}$ 262 nm, λ $_{min}^{H_2O}$ 239 nm.

2.

7-β-[D-α-(β-Methylsulfonylethoxycarbonyl)aminophenyl-acetamido]-3-formyl-3-cephem-4-carboxylic acid Acetone (16 ml.) is added to 7-β-[D-α-(β-methylsulfonylethoxycarbonyl)aminophenylacetamido]-3-hydroxymethyl-3-cephem-4-carboxylic acid sodium (535 mg.) and the resultant suspension is stirred under cooling at 5°C. Then, the oxidizing reagent A prepared according to Example 3 (0.250 ml.) is added dropwise to the suspension over a period of 3 minutes and the mixture is further stirred at 5°C for 20 minutes. After the reaction has been completed, a major portion of the acetone is distilled off under reduced pressure and water (40 ml.) is added. The mixture is then extracted twice with ethyl acetate (50 ml.). The ethyl acetate solution is dehydrated over anhydrous sodium sulfate and, then, evaporated to dryness under reduced pressure. The procedure yields 7-β-[D-α-(β-methylsulfonylethoxy-carbonyl)amino phenylacetamido]-3-formyl-3-cephem-4-carboxylic acid (266 mg.).

Nuclear magnetic resonance spectrum (d$_6$-dimethylsulfoxide + D$_2$O): δ 3.04(3H, s, —SO$_2$CH$_3$), 5.04(1H, d, J=5Hz, 6-H),

5.83(1H, d, J=5Hz, 7-H), 6.22(1H,

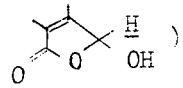

Infrared absorption spectrum (KBr disc): 1794cm$^{-1}$(β-lactam ring)

Ultraviolet absorption spectrum: λ $_{max}^{H_2O}$ 299 nm; λ $_{min}^{H_2O}$ 243 nm. λ $_{max}^{H_2O\text{-}H\ SO}$ 259 nm; λ $_{min}^{H_2O\text{-}H_2SO}$ 239 nm The nuclear magnetic resonance spectrum of this product in d$_6$-dimethylsulfoxide reveals that it takes the lactol form which is a tautomer of the 3-formylcarboxylic acid form, while the ultraviolet absorption spectrum of the same in aqueous solution shows that it exists in the 3-formylcarboxylic acid form. The ultraviolet absorption spectrum of the same product in diluted sulfuric acid reveals that it is in the lactol form.

3. In acetic anhydride (2 ml.) is dissolved 7-β-[-D-α-(β-methylsulfonylethoxycarbonyl)aminophenylacetamido]-3-formyl-3-cephem-4-carboxylic acid (204 mg.) and while the resultant solution is cooled to 5°C, a drop of pyridine is added. The solution is allowed to stand at room temperature for 1.5 hour. Then, the solution is extracted twice with ethyl acetate (15 ml.) and washed with a saturated aqueous solution of sodium chloride. The organic layers are pooled, dehydrated over anhydrous sodium sulfate and concentrated under reduced pressure. The residue is run onto a column of silica gel and eluted with ethyl acetate. The fractions are pooled and concentrated to dryness under reduced pressure, whereupon two types of acetate separate.

Nuclear magnetic resonance spectra (d$_6$-dimethylsulfoxide + D$_2$O):

α-Acetate

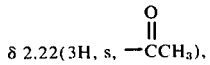

3.08(3H, s, —SO$_2$CH$_3$), 5.11(1H, d, J=5Hz, 6-H), 5.87(1H, d, J=5Hz, 7-H), 7.00(1H, s, 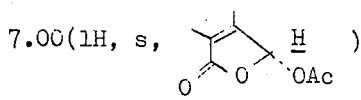 )

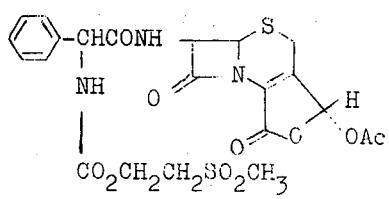

β-Acetate

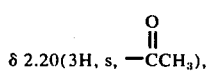

3.08(3H, s, —SO$_2$CH$_3$), 5.08(1H, d, J=5Hz, 6-H), 5.86(1H, d, J=5Hz, 7-H), 7.05(1H, s, 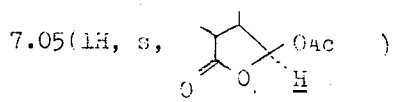 )

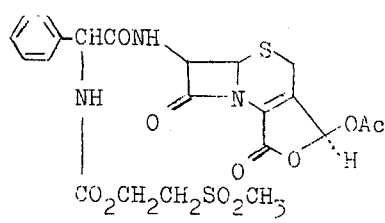

EXAMPLE 5

1.
7-β-(D-α-Sulfophenylacetamido)-3-hydroxymethyl-3-cephem-4-carboxylic acid disodium In phosphate buffer (15 ml.) is dissolved 7-β-(D-α-sulfophenylacetamido)-3-acetoxymethyl-3-cephem-4-carboxylic acid disodium (1.0 g.). After the solution is adjusted to pH 7.20, lipase "Saiken 100" (1.0 g.) is added at 30°C and the mixture is stirred for 20 hours. The reaction mixture is concentrated under reduced pressure to 5 ml. and the concentrate is chromatographed on a column of methylated dextran manufactured by Pharmacia under the tradename "Sephadex LH-20". The column is irrigated with water to remove the enzyme and the active fraction is lyophilized to obtain a while powder (2.53 g.). This product includes inorganic matters. Therefore, the product if further chromatographed on a column of Amberlite XAD-2 resin and carefully eluted with water. The inorganics-free fraction is lyophilized to harvest white powdery crystals of 7-β-(D-α-sulfophenylacetamido)-3-hydroxymethyl-3-cephem-4-carboxylic acid disodium (512 mg.).

Nuclear magnetic resonance spectrum (D$_2$O, 100MHz):

δ3.36 and 3.65 (2H, AB-pattern q, J=18Hz), 4.33(2H), 5.15(1H, d, J=5.0Hz), 5.18(1H), 5.76(1H, d, J=5.0Hz), 7.46–7.79(5H).

Infrared absorption spectrum (KBr disc): 1755 cm$^{-1}$(β-lactam ring), 1220 and 1045 cm$^{-1}$(SO$_3^-$).

2.
7-β-(D-α-sulfophenylacetamido)-3-formyl-3-cephem-4-carboxylic acid monosodium In acetone (5 ml.) is suspended 7-β-(D-α-sulfophneylacetamido)-3-hydroxymethyl-3-cephem-4-carboxylic acid disodium (225 mg.) and the resultant suspension is stirred under cooling at 5°C. To this suspension is added the reagent B according to Example 1 (0.187 ml.) over a period of 1 minute.

After the dropwise addition has been completed, the mixture is stirred for another 10 minutes and, then, the reaction mixture is concentrated under reduced pressure.

To the residue is added water (2 ml.), followed by the addition of sodium hydrogen carbonate so as to bring the pH to 2.5. The solution is then chromatographed on a column of Amberlite XAD-2 resin and desorbed with water. From the inorganic ion-free eluate, the fractions containing the contemplated product are collected and lyophilized. The procedure yields powdery crystals of 7-β-(D-α-sulfophenylacetamido)-3-formyl-3-cephem-4-carboxylic acid monosodium (106 mg.).

Nuclear magnetic resonance spectrum D$_2$O, 100 MHz): δ 3.68(2H), 5.06(1H, d, J=5Hz), 5.77(1H, d, J=5Hz), 5.18(1H), 6.22(1H, s, 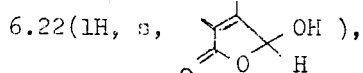 ), 7.46–7.79(5H)

EXAMPLE 6

1. N-(p-(t-butyl)-benzenesulfonyl)-cephalosporin C.

In the method of Example 1(1), p-(t-butyl-benzenesulfonyl chloride is employed instead of isobornyl chlorocarbonate and reacted at 15° – 20°C to give the objective compound.

Infrared absorption spectrum (KBr disc): 1770, 1728, 1710, 1660 cm$^{-1}$

Nuclear magnetic resonance spectrum (d$_6$-dimethylsulfoxide): δ 1.29(9H), 2.01(3H), 3.40 and 3.64(2H, ABq), 4.70 and 5.02(2H, ABq), 5.06(1H, d), 5.64(1H, q), 7.50 and 7.68(4H, ABq), 7.94(1H, d), 8.72(1H, d).

2. Disodium
7β-[5-(p-t-butylbenzenesulfonamide)-5-carboxyvaleramido]-3-hydroxymethyl-3-cephem-4-carboxylate N-(p-(t-butyl)-benzenesulfonyl)-cephalosporin C (50 g.) is reacted in a manner similar to that in Example 1 (2) and the reaction mixture is cooled down to 5°C, followed by adjusting its pH to 2.90. The solution is added 1 l. of ethyl acetate and the mixture is stirred thoroughly, followed by filtration using Celite. The Celite is washed with ethyl acetate (500 ml.) and the washing is combined with the filtrate. The ethyl acetate layer separated is washed wish water (100 ml. × 3) and added 3% aqueous solution of sodium hydrogen carbonate until the pH of its aqueous layer becomes 5.5, followed by separating the aqueous layer. The aqueous layer is adjusted its pH at 7.0 and lyophilized to give the objective compound (35.6 g.). Infrared absorption spectrum (KBr disc): 1754, 1660, 1595 cm$^{-1}$.

Nuclear magnetic resonance spectrum (D$_2$O): δ 1.30(9H), 4.36(2H), 5.15(1H, d), 5.68(1H, d), 7.60 and 7.86(4H, ABq).

3.

7β-[5-(p-t-butylbenzenesulfonamido)-5-carboxyvaleramido]-9-oxo-11-hydroxy-11H-furano[4,3-c]-3-cephem The hydroxymethyl derivative obtained in above (2) is treated in a manner similar to that in Example I (3) to give the objective compound. Infrared absorption spectrum (KBr disc): 1788, 1728, 1665, 1534, 1323, 1158 cm$^{-1}$.

Nuclear magnetic resonance spectrum (d$_6$-DMSO): δ 1.29(9H, s), 1.3–1.9(6H, m), 3.4–3.8 (2H, m), 5.06(1H, d, J=5Hz), 5.80(1H, q, J=5 and 8Hz), 6.24

(1H, broad s, 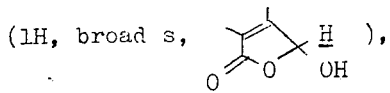 ), 7.51(2H, d, J=8Hz), 7.69(2H, d, J=8Hz), 7.93(1H, d, J=8Hz), 8.80(1H, d, J=8Hz).

EXAMPLE 7

1. N-benzoyl-3-deacetylcephalosporin C disodium

N-benzoylcephalosporin C is treated in a manner similar to that in Example 1 (2) to give the objective compound. Infrared absorption spectrum (KBr disc): 1757, 1645, 1600, 1535 cm$^{-1}$.

Nuclear magnetic resonance spectrum (D$_2$O): δ 1.90(4H, m), 2.50(2H, m), 3.30 and 3.65(2H, ABq), 4.33(2H), 5.15(1H, d), 5.68(1H, d), 7.63(3H), 7.90(2H).

Ultraviolet absorption spectrum: $\lambda_{max}^{H_2O}$ 230, 260 nm.

2.

7β-(5-benzamido-5-carboxyvaleramido)-9-oxo-11-hydroxy-11H-furano[4,3-c]-3-cephem N-benzoyl-3-deacetylcephalosporin C disodium is treated in the same manner as in Example 1 (3) to give the objective compound.

Infrared absorption spectrum(KBr disc): 1790, 1730, 1641, 1535 cm$^{-1}$.

Nuclear magnetic resonance spectrum(d$_6$-DMSO): δ 1.40–1.90(4H, m), 2.00–2.40(2H, m), 3.45 and 3.76 (2H, ABq, J=18Hz), 4.37(1H, m), 5.05(1H, d, J=5Hz), 5.82(1H, q, J=5 and 8 Hz), 6.24(1H, m, 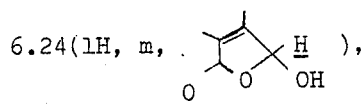 ), 7.30–7.55(3H, m), 7.75–8.00(2H, m), 8.55(1H, d, J=8Hz), 8.90(1H, d, J=8Hz).

Ultraviolet absorption spectrum: $\lambda_{max}^{H_2O}$ 302 nm.

EXAMPLE 8

1. N-Tosyl-3-deacethylcephalosporin C disodium

N-Tosylcephalosporin C disodium is treated in a manner similar to that in Example 1 (2) to give the objective compound.

Infrared absorption spectrum (KBr disc): 1760, 1160 cm$^{-1}$.

Nuclear magnetic absorption spectrum (D$_2$O): δ 1.6–1.9(4H, m), 2.1–2.5(2H, m), 2.49(3H), 3.6(1H), 3.49 and 3.74(2H, ABq), 4.35(2H), 5.16(1H, d), 5.63 (1H, d), 7.47(2H, d), 7.80(2H, d).

2.

7β-(5-Tosylamido-5-carboxyvaleramido)-9-oxo-11-hydroxy-11H-furano[4,3-C]-3-cephem N-Tosyl-3-desacethylcephalosporin C disodium is treated in the similar manner as Example 1 (3) to give the objective compound.

Melting point: 157°–160°C (decomp.)

Infrared absorption spectrum(KBr disc): 1800, 1160 cm$^{-1}$.

Nuclear magnetic resonance spectrum(d$_6$-DMSO, 100 MHz): δ 1.4–1.9(4H, m, —(CH$_2$) 2—), 1.9–2.3(2H,m,—CH$_2$—), 2.34(3H, s, CH$_3$), near 3.65(3H, s, 2-CH$_2$, and methin) 5.04(1H, d, J=5.0Hz), 5.20(1H, broad s, 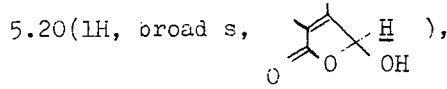 ), 5.77(1H, q, J=9 and 5Hz).

Elementary analysis: Found: C, 47.19; H, 4.32; N, 7.40. Calcd. (for C$_{21}$H$_{24}$N$_3$O$_9$S$_2$): C, 47.99; H, 4.41; N, 8.00.

EXAMPLE 9

1. N-(p-(t-butyl)-benzoyl)-cephalosporin C

In the method of Example 1 (1), p-(t-butyl)-benzoyl chloride is employed instead of isobornyl chlorocarbonate and reacted at 15°C to give the objective compound.

Infrared absorption spectrum (KBr disc), 1778, 1730, 1708, 1680, 1660, 1540 cm$^{-1}$.

Nuclear magnetic resonance spectrum (d$_6$-dimethylsulfoxide); δ 1.28(9H), about 1.5–1.9(4H), 2.01(3H), 2.10–2.35 (2H), 3.36 and 3.61(2H, ABq), 4.37(1H), 4.68 and 4.99 (2H, ABq), 5.06(1H), 5.67(1H), 7.46 and 7.82(4H, ABq), 8.41(1H), 8.79(1H). 2. Disodium 7β-[5-(p-t-butylbenzamido)-5-carboxyvaleramido]-3-hydroxymethyl-3-cephem-4-carboxylate N-[p-(t-butyl)-benzoyl]-cephalosporin C is treated in a manner similar to that in Example 3 (1) to give the objective compound.

Infrared absorption spectrum (KBr disc); 1760 cm$^{-1}$

Nuclear magnetic reasonance spectrum (D$_2$O): δ 1.25(9H), 3.27 and 3.57(2H, ABq), 4.30(2H), 5.07 (1H), 5.68(1H), 7.50 and 7.84(4H, ABq).

3.

7β-[5-(p-t-butylbenzamido)-5-carboxyvaleramido]-9-oxo-11-hydroxy-11H-furano[4,3-c]-3-cephem Disodium 7β-(5-(p-t-butylbenzamido)-5-carboxyvaleramido]-3-hydroxymethyl-3-cephem-4-carboxylate is treated in a manner similar to that in Example 3(2) to give the objective compound.

Infrared absorption spectrum (KBr disc): 1790, 1730, 1640, 1534 cm$^{-1}$.

Nuclear magnetic resonance spectrum d$_6$-DMSO): δ 1.29(9H, s), 1.50–1.95(4H, m), 2.10–2.40(2H, m), 3.36 and 3.58(2H, ABq), 4.36(1H, m), 5.06(1H, d, J=5Hz), 5.60(1H, m, 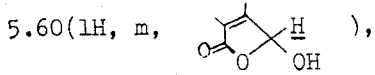 ), 5.81(1H, q, J=5 and 8 Hz), 7.45 and 7.83(4H, ABQ, J=8Hz), 8.43(1H, d, J=8Hz), 8.86(1H, d, J=8Hz).

What we claim is:

1. A process for preparing a product compound having the formula

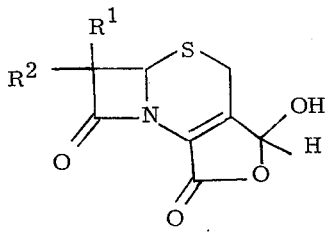

wherein R¹ is hydrogen, methoxy or ethoxy, and R² is an amino group acylated with a member selected from the group consisting of hexanoyl, propionyl, heptanoyl, cyclopentanoyl, phenylacetyl, cyclohexylacetyl, thienylacetyl, tetrazolylacetyl, cyanoacetyl, phenoxyacetyl, nitrophenylacetyl, phenylthioacetyl, phenethylthioacetyl, allylthioacetyl, benzylthiopropionyl, α-carboxyphenylacetyl, α-bromopropionyl, α-sulfothienylacetyl, α-sulfophenylacetyl, α-hydroxyphenylacetyl, α-phenoxybutyloyl, phenylglycyl, cyclohexenylglycyl, thienylglycyl, furylglycyl, phenylmethylglycyl, carbamoylphenylacetyl, 5-amino-5-carboxyvaleryl, 5-benzoylamino-5-carboxyvaleryl, 5-(isobornyloxycarbonyl)-amino-5-carboxyvaleryl, α(β-methylsulfonylethoxycarbonyl)-aminophenylacetyl, 5-(β-methylsulfonylethoxycarbonyl)amino-5-carboxyvaleryl, 5(phenylacetyl)amino-5-carboxyvaleryl, 5-[p-(t-butyl)-benzoylsulfonyl]amino-5-carboxyvaleryl, 5-tosylamino-5-carboxyvaleryl, 5-p-(t-butyl)-benzoylamino-5-carboxyvaleryl, acryl, benzoyl, 2,6-dimethoxybenzoyl, 5-methyl-3-phenyl-4-isoxazolylcarbonyl and 3-0-chlorophenyl-5-methyl-5-isoxazolylcarbonyl or an imido group from the group consisting of phthalimido, succinimido and maleinimido, said process comprising directly oxidizing a starting compound having the formula

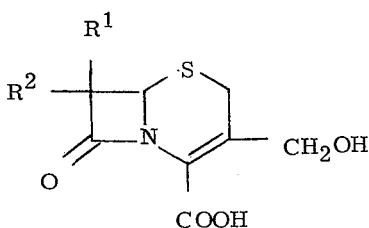

wherein R¹ and R² are the same as defined above, or an alkali metal salt, triethylamine salt or pyridine salt thereof in a solvent therefor, direct oxidation being carried out with an oxidation agent comprising a hexavalent chromium compound selected from the group consisting of chromic anhydride, chromic acid t-butyl ester, chromyl acetate and chromyl chloride, direct oxidation being carried out at a temperature of about 0° to 30°C at a pH close to the pKa of the 4-carboxylic group of said starting compound.

2. A process for preparing a product compound having the formula

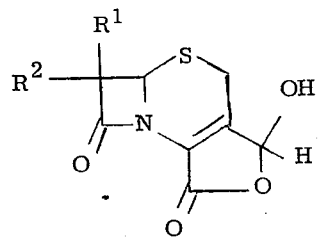

wherein R¹ is hydrogen, methoxy or ethoxy, and R² is an amino group acylated with N-protected 5-amino-5-carboxyvaleryl, said process comprising directly oxidizing a starting compound having the formula

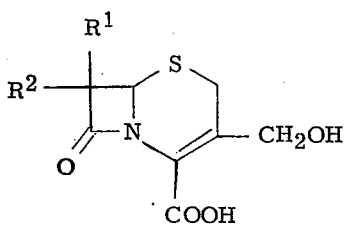

wherein R¹ and R² are the same as defined above, or an alkali metal salt, triethylamine salt or pyridine salt thereof in a solvent therefor, direct oxidation being carried out with an oxidation agent comprising a hexavalent chromium compound selected from the group consisting of chromic anhydride, chromic acid t-butyl ester, chromyl acetate and chromyl chloride, direct oxidation being carried out at a temperature of about 0° to 30°C at a pH close to the pKa of the 4-carboxylic group of said starting compound 3. A process according to claim 1, wherein R¹ represents hydrogen.

4. A process according to claim 1, wherein R² is an N-protected 5-amino-5-carboxyvalerylamino group having a protective group selected from the group consisting of benzoyl, isobornyloxycarbonyl, β-methylsulfonylethoxycarbonyl, phenylacetyl, p-(t-butyl)-benzenesulfonyl, tosyl and p-(t-butyl)-benzoyl group.

5. A process according to claim 1 wherein the solvent is an organic solvent.

6. A process according to claim 5, wherein the organic solvent is selected from the group consisting of acetone, acetonitrile, tetrahydrofuran, ethyl acetate, chloroform, dichloromethane, ether dioxane, dimethylfomamide, dimethylacetamide, acetic acid and mixtures thereof.

7. A process according to claim 5, wherein the organic solvent is substantially anhydrous.

8. A process according to claim 1, wherein said starting compound is in the form of a salt.

9. A process according to claim 8, wherein the hexavalent chromium compound is reacted in the presence of an acid, the ratio of hexavalent chromium compound (per oxidation equivalent): acid (per mole): the starting compound to be oxidized being 2:n:1 wherein n is the number of acid groups in said starting compound.

10. A process according to claim 1, wherein said hexavalent chromium compound is chromic anhydride.

11. A process according to claim 9, wherein the acid is selected from the group consisting of sulfuric acid, phosphoric acid and glacial acetic acid.

12. A process according to claim 9, wherein the acid is concentrated sulfuric acid.

13. A process according to claim 1, wherein $R^1$ represents hydrogen or methoxy group.

14. The process according to claim 1, wherein the reaction is effected in the presence of acid.

15. A process according to claim 14, wherein the amount of acid is sufficient so that the pH of the reaction system is about 2.9.

16. A compound represented by the general formula:

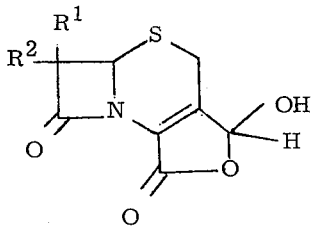

wherein $R^1$ is hydrogen, methoxy or ethoxy, and wherein $R^2$ is an amino group acylated with a member selected from the group consisting of hexanoyl, propionyl, heptanoyl, cyclopentanoyl, phenylacetyl, cyclohexylacetyl, thienylacetyl, tetrazolylacetyl, cyanoacetyl, phenoxyacetyl, nitrophenylacetyl, phenylthioacetyl, phenethylthioacetyl, allylthioacetyl, benzylthiopropionyl, α-carboxyphenylacetyl, α-bromopropionyl, α-sulfothienylacetyl, α-sulfophenylacetyl, α-hydroxyphenylacetyl, α-phenoxybutyloyl, phenylglycyl, cyclohexedylglycyl, thienylglycyl, furylglycyl, phenylmethylglycyl, carbamoylphenylacetyl, 5-amino-5-carboxyvaleryl, 5-benzoylamino-5-carboxyvaleryl, 5-(isobornyloxycarbonyl)-amino-5-carboxyvaleryl, α-(β-methylsulfonylethoxycarbonyl)-aminophenylacetyl, 5-(β-methylsulfonylethoxycarbonyl)amino-5-carboxyvaleryl, 5-(phenylacetyl)amino-5-carboxyvaleryl, 5-[p-(t-butyl)-benzoylsulfonyl]amino-5-carboxyvaleryl, 5-tosylamino-5-carboxyvaleryl, 5-p-(t-butyl)-benzoylamino-5-carboxyvaleryl, acryl, benzoyl, 2,6-dimethoxybenzoyl, 5-methyl-3-phenyl-4-isoxazolylcarbonyl and 3-0-chlorophenyl-5-methyl-4-isoxazolylcarbonyl or an imido group selected from the group consisting of phthalimido, succinimido and maleinimido.

17. A compound according to claim 16, wherein $R^1$ is hydrogen and $R^2$ is an amino group acylated with 5-(isobornyloxycarbonyl)-amino-5-carboxyvaleryl.

18. A compound according to claim 16, wherein $R^1$ is hydrogen and $R^2$ is an amino group acylated with 5-(phenylacetyl) amino-5-carboxyvaleryl.

19. A compound according to claim 16, wherein $R^1$ is hydrogen and $R^2$ is an amino group acylated with 2-thienylacetyl.

20. A compound according to claim 16, wherein $R^1$ is hydrogen and $R^2$ is an amino group acylated with α-(β-methylsulfonylethoxycarbonyl)-aminophenylacetyl.

21. A compound according to claim 16, wherein $R^1$ is hydrogen and $R^2$ is an amino group acylated with α-sulfophenylacetyl.

22. A compound according to claim 16, wherein $R^1$ is hydrogen and $R^2$ is an amino group acylated with 5-[p-(t-butyl)-benzenesulfonyl]amino-5-carboxyvaleryl.

23. A compound according to claim 16, wherein $R^1$ is hydrogen and $R^2$ is an amino group acylated with 5-benzoylamino-5-carboxyvaleryl.

24. A compound according to claim 16, wherein $R^1$ is hydrogen and $R^2$ is an amino group acylated with 5-tosylamino-5-carboxyvaleryl.

25. A compound according to claim 16, wherein $R^1$ represents hydrogen or methoxy group.

26. A compound according to claim 16, wherein $R^1$ represents hydrogen.

27. A compound according to claim 16, wherein $R^2$ is an N-protected 5-amino-5-carboxyvalerylamino group having a protective group selected from the group consisting of benzoyl, isobornyloxy-carbonyl, β-methylsulfonylethoxycarbonyl, phenylacetyl, p-(t-butyl)-benzenesulfonyl, toxyl and p-(t-butyl)-benzoyl group.

28. A compound represented by the general formula:

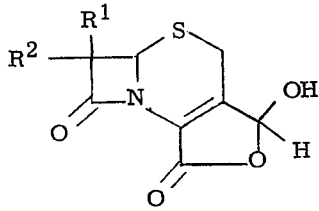

wherein $R^1$ is hydrogen, methoxy or ethoxy, and wherein $R^2$ is an amino group acylated with N-protected 5-amino-5-carboxyvaleryl.

29. 7β-[5-(p-t-butylbenzamido)-5-carboxyvaleramido]-9-oxo-11-hydroxy-11H-furano[4,3-c]-3-cephem.

* * * * *